US009107731B2

(12) United States Patent
Reinstein et al.

(10) Patent No.: US 9,107,731 B2
(45) Date of Patent: Aug. 18, 2015

(54) METHOD FOR INCREASING OCULAR DEPTH OF FIELD

(75) Inventors: Dan Z. Reinstein, London (GB); Hartmut Vogelsang, Jena (DE); Michael Bergt, Weimar (DE)

(73) Assignee: CARL ZEISS MEDITEC AG, Jena (DE)

(*) Notice: Subject to any disclaimer, the term of this patent is extended or adjusted under 35 U.S.C. 154(b) by 1016 days.

(21) Appl. No.: 13/225,590

(22) Filed: Sep. 6, 2011

(65) Prior Publication Data
US 2012/0078239 A1     Mar. 29, 2012

Related U.S. Application Data

(60) Provisional application No. 61/380,067, filed on Sep. 3, 2010.

(51) Int. Cl.
*A61F 9/008*     (2006.01)

(52) U.S. Cl.
CPC ......... *A61F 9/00804* (2013.01); *A61F 9/00806* (2013.01); *A61F 2009/0088* (2013.01); *A61F 2009/00857* (2013.01); *A61F 2009/00859* (2013.01); *A61F 2009/00872* (2013.01); *A61F 2009/00897* (2013.01)

(58) Field of Classification Search
CPC ................. A61F 9/008; A61F 2009/00872
USPC .................. 606/4, 5; 351/159.01–159.03
See application file for complete search history.

(56) References Cited

U.S. PATENT DOCUMENTS

| 2003/0153904 | A1* | 8/2003 | Patel ................................ 606/5 |
| 2003/0208190 | A1* | 11/2003 | Roberts et al. ..................... 606/5 |
| 2005/0107775 | A1* | 5/2005 | Huang et al. ...................... 606/5 |
| 2006/0195074 | A1* | 8/2006 | Bartoli ............................... 606/4 |
| 2006/0235369 | A1* | 10/2006 | MacRae et al. .................... 606/4 |
| 2007/0279585 | A1* | 12/2007 | Bartoli .......................... 351/161 |
| 2010/0076423 | A1* | 3/2010 | Muller ............................ 606/33 |
| 2010/0211054 | A1* | 8/2010 | Lemonis ........................... 606/5 |

OTHER PUBLICATIONS

Dan Z. Reinstein et al., LASIK for Hyperopic Astigmatism and Presbyopia Using Micro-monovision With the Carl Zeiss Meditec MEL80 Platform, Journal of Refractive Surgery, vol. 25, Jan. 2009, pp. 37-58.
Dan Z. Reinstein et al., LASIK for Myopic Astigmatism and Presbyopia Using Non-linear Aspheric Micro-monovision With the Carl Zeiss Meditec MEL 80 Platform, Journal of Refractive Surgery, vol. 27, No. 1, 2011, pp. 23-37.

* cited by examiner

*Primary Examiner* — William Thomson
*Assistant Examiner* — Jeffrey Lipitz
(74) *Attorney, Agent, or Firm* — Leydig, Voit & Mayer, Ltd.

(57) ABSTRACT

A method for performing a corneal ablation procedure on an eye of a patient including determining a refractive correction for the eye and determining a first parameter corresponding to the refractive correction or a condition of the patient. An ablation profile is selected that includes a refractive correction component and a pre-compensating component that is selected based on the first parameter. The ablation profile is configured to promote a controlled induction of a higher order aberration, where the pre-compensating component limits the induction of the higher order aberration to be within a pre-defined range. The cornea is ablated using the selected ablation profile.

4 Claims, 5 Drawing Sheets
(3 of 5 Drawing Sheet(s) Filed in Color)

METHOD FOR INCREASING OCULAR DEPTH OF FIELD

CROSS REFERENCE TO RELATED APPLICATIONS

This application claims priority under 35 U.S.C. §119(e) to provisional Patent Application Ser. No. 61/380,067, filed Sep. 3, 2010, which is hereby incorporated by reference herein in its entirety.

BACKGROUND

Spherical aberration (SA) and other higher order aberrations (HOA) can be beneficial to a person's vision because it can result in an increase in depth of field. SA is a naturally occurring aberration in all human eyes, and as a result, the visual cortex has developed the ability to process a retinal image that has been slightly degraded by the presence of spherical aberration to sharpen the perceived image. Depth of field is increased by the ability of the visual cortex to process spherical aberration, and allow objects to be perceived to be in focus over a greater range of focal distances. Both negative and positive spherical aberration have a similar effect of increasing depth of field.

While some SA is beneficial, too much spherical aberration can be detrimental to the quality of vision. For example, patients with too much spherical aberration can experience decreased contrast sensitivity and night vision disturbances. The inventors of the present application have concluded that there is a maximum tolerable level of SA above which the brain's natural neural processing can no longer sharpen the retinal image to produce a clear perceived image in the mind.

Corneal excimer laser ablation profiles induce spherical aberration because of healing and biomechanical responses such as, e.g., paracentral stromal thickening and epithelial thinning, and to a lesser extent uncertainties in the ablation, e.g., due to fluence and projection. The amount of induced spherical aberration caused by the laser ablation profile is correlated to the magnitude of refraction treated, where higher refractions induce more spherical aberration. The correction of myopic refraction induces negative spherical aberration, whereas the correction of hyperopic refraction induces positive spherical aberration (using Malacara notation).

The effects of inducing spherical aberration and other higher order aberrations can also be important in patients that have been implanted with an intraocular lens (IOL). An IOL is an implanted lens in the eye to typically replace the existing crystalline lens because it has been clouded over by a cataract. Alternatively, an IOL may be implanted as a form of refractive surgery to change the optical power of the eye and correct for refractive errors. The IOL usually consists of a small synthetic lens with side struts, which are commonly referred to as haptics and are useful in holding the lens in place within the capsular bag or posterior chamber or anterior chamber of the eye. Modern IOL are made of flexible materials and are typically configured as fixed monofocal lenses designed to correct distance vision to plano although other types are available, such as multifocal IOLs and accommodative IOLs. Even though IOLs enable many patients to reduce their dependence on glasses, most patients still rely on glasses for certain activities, such as reading.

U.S. Patent Application Publication No. 2006/0195074 A1, to Bartoli describes an excimer LASER unit and relative control method for performing corneal ablation for partially correcting presbyopia that includes introducing an amount of SA to the eye of a subject. Although this and other similar methods are generally supportive to patient's vision, the uncontrolled induction of SA, for example, as described by Bartoli, has been known to result in poor contrast sensitivity for some patients, un-tolerated loss of visual acuity for far vision, or non-beneficial blur at different viewing distances.

SUMMARY

In an embodiment, the present invention provides a method for performing a corneal ablation procedure on an eye of a patient including determining a refractive correction for the eye and determining a first parameter corresponding to the refractive correction or a condition of the patient. An ablation profile is selected that includes a refractive correction component and a pre-compensating higher order aberration component that is selected based on the first parameter. The ablation profile is configured to promote a controlled induction of higher order aberration, where the pre-compensating component limits the induction of higher order aberration to be within a predefined range. The cornea is ablated using the selected ablation profile.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee. Embodiments of the present invention are described in more detail below with reference to the drawings, in which.

DETAILED DESCRIPTION

Figure 1:
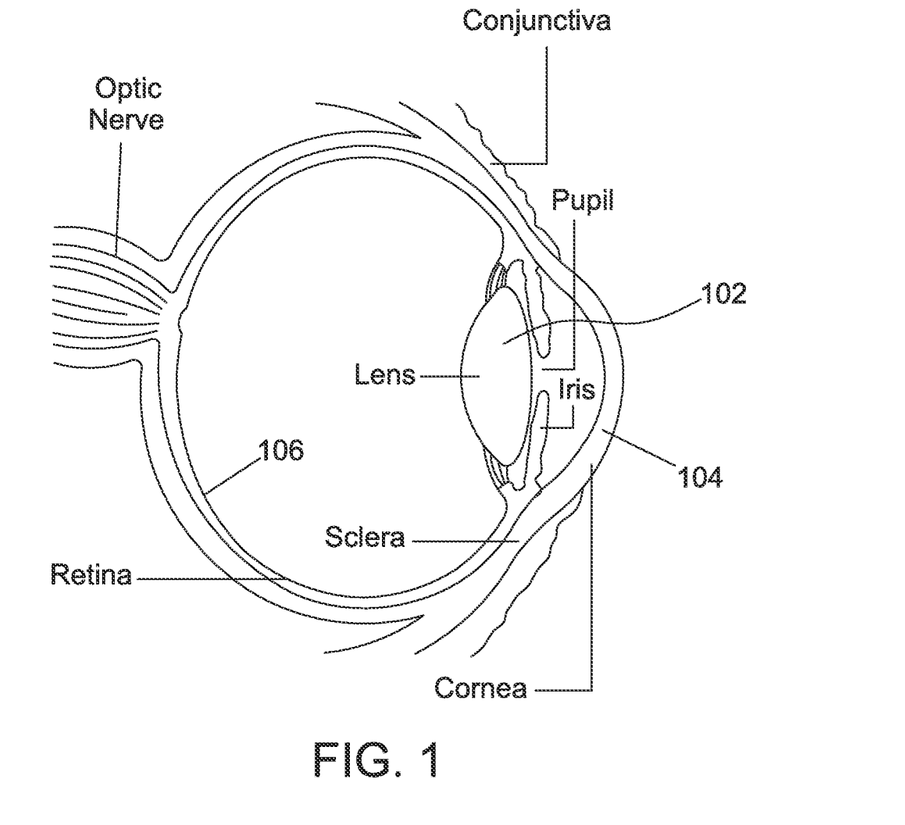
FIG. 1 is a schematic section of an eye.

The present invention is directed to methods and systems relating to procedures performed on an eye. FIG. 1 shows a schematic section of an eye to illustrate certain parts of the eye that are particularly relevant to the methods described herein. In particular, light entering the eye passes through the cornea 104 and then through the lens 102 before reaching the retina 106. The cornea is made of five layers including the epithelial layer of approximately 53 µm in thickness overlying the stroma, which is approximately 500 µm in thickness.

In an embodiment, the present invention provides a method of controlling one or more higher order aberrations that are induced during a medical procedure performed on a patient's eye. The aberrations that are induced may include spherical aberrations or other higher order aberrations, e.g., trefoil, coma, quadrafoil and secondary astigmatism. In particular, the method can achieve an induction of higher order aberration (either positive or negative) that leaves the patient with a post-operative amount of higher order aberration at a specific target or within a desirable range where the depth of field is increased without negatively affecting the quality of vision.

In an embodiment of the invention, the control of higher order aberrations is achieved by including a component in the ablation profile that pre-compensates for the higher order aberration that is induced by the ablation procedure. Higher order aberrations can be described using mathematical reconstruction algorithms based on Zernike polynomials, Fourier transformations or others expansions. Zernike polynomials are commonly used for wavefront reconstructions in ophthalmology as many of the Zernike terms relate to clinically relevant optical effects. For example, the $Z_4^0$ term is a direct description of spherical aberration. Therefore, including a $Z_4^0$ component into the ablation profile can be used to pre-compensate for the expected spherical aberration induction due to the ablation, or to induce further spherical aberration. Other Zernike coefficients including the $Z_6^0$ term can also be included to control the induction of spherical aberration. In the description that follows, reference to positive or negative $Z_4^0$ values is made in accordance with the Malacara notation.

In one embodiment of the disclosed method, the analysis and determination of the aberrations is performed relative to the corneal vertex and not the pupil centre. This is because the corneal vertex is a better approximation of the visual axis, which more closely represents the patient's vision as it is the line joining the fixation point and the foveal image through the nodal points. The corneal ablation profile can also be centered on the corneal vertex. Thus, the corrective higher order aberration, such as spherical aberration, is applied centered to the corneal vertex. This is an improvement over previous systems in which profiles were centered on the entrance pupil center. Centration of the corrective higher order aberration is more effective on the corneal vertex than on the pupil centre because the aberrations are induced symmetrically about the visual axis will increase depth of field. In contrast, induction of aberrations centered on the entrance pupil centre would result in a smaller amount of spherical aberration being induced on the corneal vertex and therefore less depth of field for the optical system of the eye and can also result side effects such as smearing and distortion of images.

The magnitude of the pre-compensating component of the ablation profile, for example, the amount of $Z_4^0$ to include in the ablation profile where the pre-compensating component includes spherical aberration, can be calculated according to a number of factors or parameters in order to increase the spherical aberration and thereby increase depth of field, without exceeding the tolerable spherical aberration threshold above which quality of vision may be reduced. Preferably, a significant parameter used to determine the magnitude of the pre-compensating component is the magnitude of the refractive correction, such that the magnitude of the component, for example, the $Z_4^0$ component, included in the ablation profile, is increased as the refractive correction is increased. As set forth above, the expected magnitude of the induction of spherical aberration resulting from the ablation is correlated with the magnitude of the refraction being treated. Accordingly, in order to keep the post-op spherical aberration within the desired tolerable range, the magnitude of the pre-compensating component can also be increased in correlation with the magnitude of the refraction being treated. The expected induction of $Z_4^0$ is calculated from the regression line between refraction treated and spherical aberration induced derived from historical clinical data, which as previously discussed includes induction of negative spherical aberration for myopia and induction of positive spherical aberration for hyperopia. However, wavefront guided ablations are known to only achieve an effective correction of approximately 30% of the $Z_4^0$ component. Therefore, the $Z_4^0$ component to use in the ablation profile is calculated as a multiple of the expected $Z_4^0$ induction such that the expected postoperative spherical aberration does not exceed the tolerable threshold.

Another parameter that can be used to determine the magnitude of the pre-compensating component is the patient's preoperative spherical aberration or other higher order aberrations, since, for example, myopic patients with high negative preoperative spherical aberration are starting nearer to the tolerable threshold, and hence require a larger pre-compensating or $Z_4^0$ component. On the other hand, if a myopic patient has positive spherical aberration, it is not necessary to include this factor in determining the ablation profile because the inclusion of a component directed to treating the positive spherical aberration could result in inducing additional negative spherical aberration and potentially exceeding the tolerable threshold. Alternatively, it is also possible to consider the positive spherical aberration when determining the magnitude of the pre-compensating spherical aberration component. The opposite is true for hyperopic patients.

The inventors found that the inclusion of the pre-compensating component in the ablation profile can have an impact on the spherical refractive correction of the profile when the magnitude of the pre-compensating component is large. While theoretical calculations predicted that including spherical aberration would affect the spherical refraction, the measured change in spherical refraction was significantly different to the prediction, and thus, it is likely that it is caused by biomechanical changes within the eye during and/or after the operation. To address this alteration of the spherical refractive correction, an embodiment of the present invention includes the consideration of the magnitude of the pre-compensating component to determine a spherical refractive correction component of the ablation profile.

Figure 2:
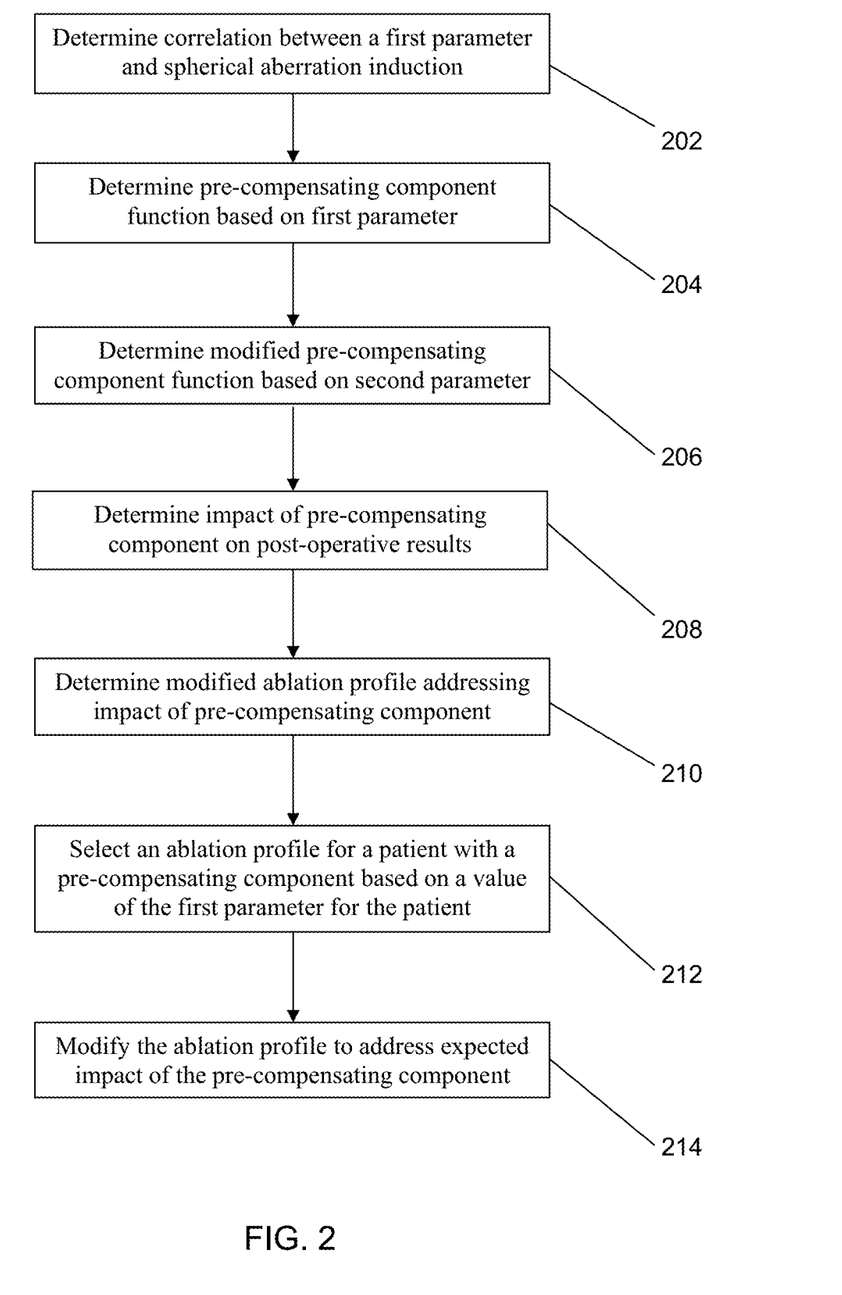
FIG. 2 is a flowchart for a method in accordance with the disclosure.

In another embodiment, the present invention provides a process for determining ablation profiles for a range of patients that allow for the induction of a higher order aberration in order to increase depth of field while controlling the induction to be within a beneficial range. An embodiment of this method relating to spherical aberration is illustrated by the flow chart in FIG. 2, however the method also applies to other higher order aberrations. In a first step 202, clinical data is analyzed to determine a correlation between a first parameter, and optionally additional parameters, and an amount of induction of spherical aberration resulting from a corneal ablation procedure. The parameters can include characteristics of the corneal ablation procedure that was performed, such as the refractive correction, biological characteristics of the eye, such as the pre-op wavefront aberration, simulated keratometry values or general information about the patient, such as age or gender. A function of a pre-compensating spherical aberration component for including in an ablation profile is then determined in 204 based on the first parameter, where the pre-compensating component is configured to control spherical aberration induction in order to prevent the post-op spherical aberration from exceeding a desired threshold. Additional modifications to the pre-compensation component function can be determined and correlated with one or more secondary parameters, such as the pre-op wavefront or patient age in 206. Additional clinical data may then be collected using ablation profiles that include the pre-compensating component and analyzed in 208 to determine any additional consequences in the post-op results that were yielded by the inclusion of the pre-compensating spherical aberration component. For example, the impact of the pre-compensating component on the spherical refractive condition can be determined. In 210 a modified ablation profile can be determined that address the additional consequences of the pre-compensating component. Steps 208 and 210 can be carried out one or more additional times in an iterative process to further refine the ablation profile. For example, a nomogram can be determined to correlate the ablation profiles with the post-op refractive correction and spherical aberration. In addition to analyzing the data and determining a correlation for the pre-compensation component based on one or more parameter values in 202 through 210, the process can also include the selection of a specific profile for an individual patient. Thus, in 212, an ablation profile can be selected for a particular patient with a pre-compensation component based on the first parameter and optionally any additional parameters. Modifications to the ablation profile can be added in 214 to address any expected impacts determined in 208 that the pre-compensating component will have on the post-operative result.

Figure 3:
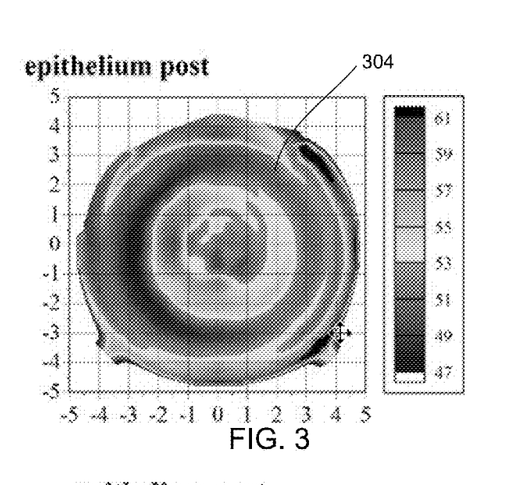
FIGS. 3-6 are topographies and epithelial thickness profiles of eyes in treatment in accordance with the disclosure.
Figure 4:
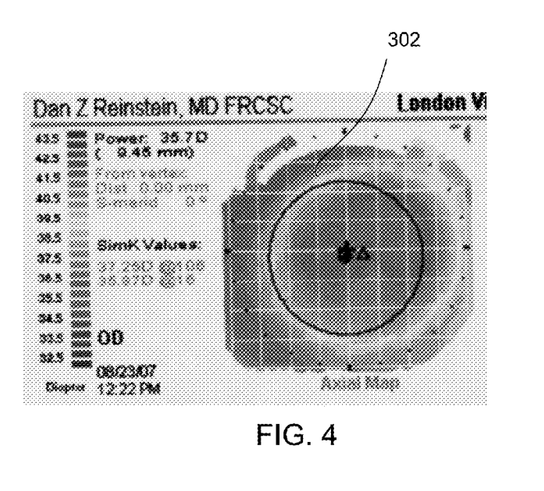

In accordance with another embodiment of the invention, the pre-compensating, such as the $Z_4^0$ component in the ablation profile also provides an added benefit due to the epithelial response. The $Z_4^0$ component of the ablation profile effectively carves a ring paracentrally in the stroma, which is then compensated for by the natural epithelial response by thickening over the location of the $Z_4^0$ ablation and thinning over the relatively steeper central region. This is an example of how the epithelium alters its thickness profile to try and re-establish a smooth, symmetrical optical surface to compensate for changes to the stromal surface. An example of this is shown in FIGS. 3 and 4 where the post-op topography and epithelial thickness profile are presented for an eye after a −10.00 D correction using an ablation profile that included a $Z_4^0$ component as described above. The post-op topography (FIG. 4) shows a perfectly smooth outer corneal surface with a large optical zone 302, however the epithelial thickness map (FIG. 3) demonstrates a ring-shaped lenticule of epithelium 304, produced by epithelial filling of the trough created paracentrally by the $Z_4^0$ ablation and epithelial thinning over the central zone of relative steepening. These epithelial thickness changes can be sufficient to fully compensate for the $Z_4^0$ irregularity on the stromal surface such that the front corneal surface is smooth and regular. Thus, the epithelium effectively acts similar to a multifocal array lens overlying the stroma due to the difference in refractive index between epithelium and stroma (1.401 vs 1.377). The multifocal properties of this epithelial lenticule are mild, and do not cause reduction in contrast sensitivity because of the adaptive nature of neural processing; however, the multifocality is beneficial at the retinal plane (surface) for imaging of objects at multiple distances (multi-focality).

Figure 5:
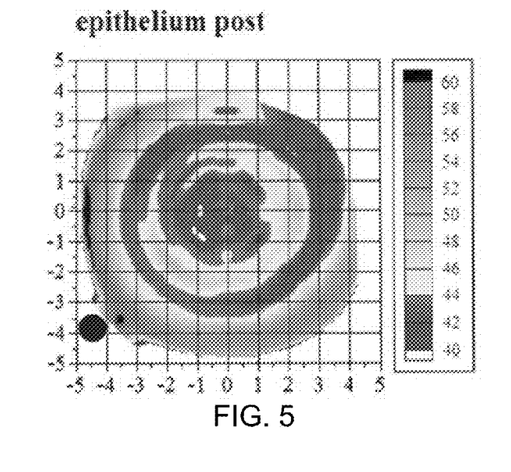
Figure 6:
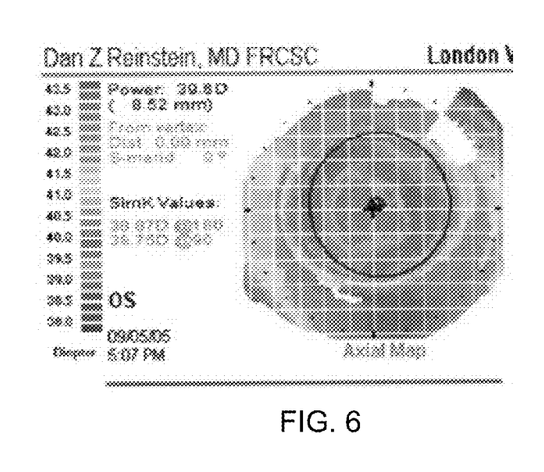

However, there is a limit to the amount of compensatory changes that the epithelium is capable of Therefore, once the $Z_4^0$ ablation is great enough such that epithelial changes cannot fully compensate for the $Z_4^0$ irregularity on the stromal ablation, then the irregularity will start to become apparent on the front corneal surface, commonly described as a central island. Topographic central islands are known to decrease visual quality, so the limit of epithelial compensation defines the safe limit for the amount of $Z_4^0$ that can be included in an ablation profile. An example of this is shown in FIGS. 5 and 6 where the post-op topography and epithelial thickness profile are presented for an eye after a high myopic ablation that included a $Z_4^0$ component of −3.00 μm. A doughnut-shaped epithelial lenticule was seen in the epithelial thickness map (FIG. 5), similar to that seen in FIG. 3, which demonstrates the amount of the stromal irregularity that had been masked from the front surface topography. However, the post-op topography (FIG. 6) shows a central area of steepening, known as a central island, which demonstrates that the epithelium was not able to fully compensate for the stromal irregularity. Studies determined that the threshold for safe use of a $Z_4^0$ component in an ablation profile to avoid the creation of a central island in the majority of eyes was found to be −3.00 μm. Accordingly, a maximum depth of the $Z_4^0$ component can be set at −3.00 μm, or more preferably, −2.75 μm.

Figure 7:
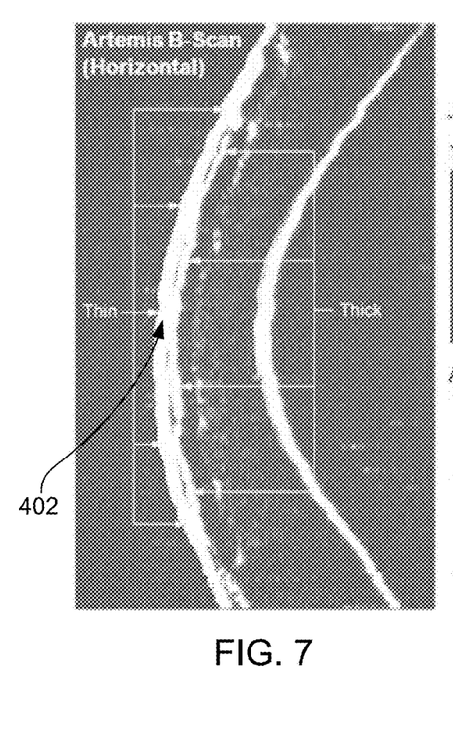
FIGS. 7-12 are various charts including topographies and sections of eyes treated in accordance with the disclosure.
Figure 8:
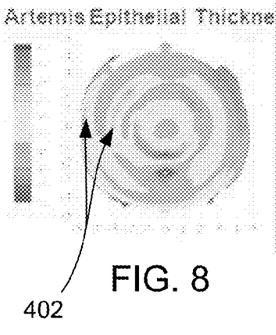
Figure 9:
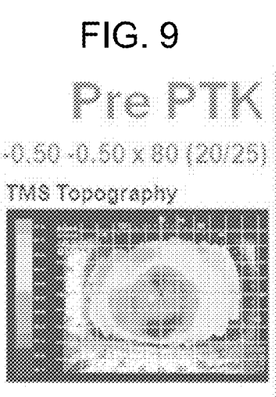
Figure 10:
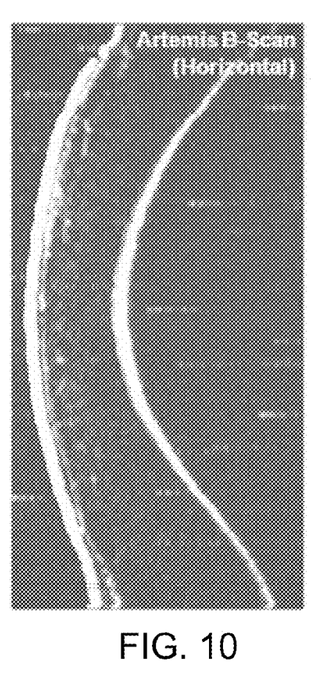
Figure 11:
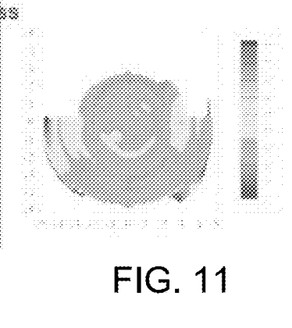
Figure 12:
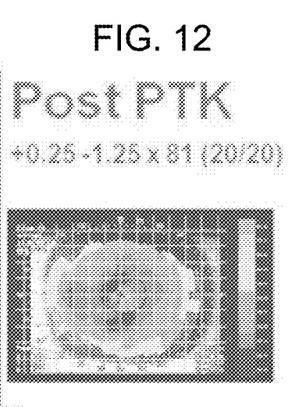
Figure 13:
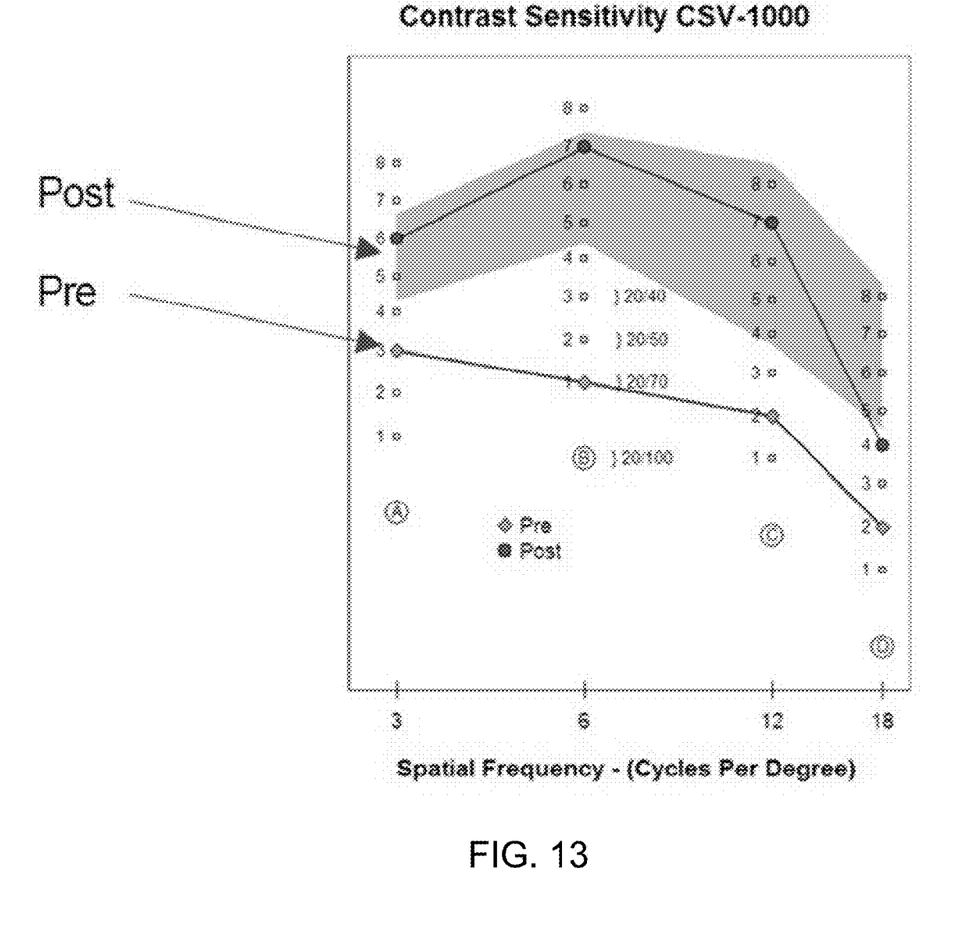
FIG. 13 is a contrast sensitivity chart for a subject treated in accordance with the disclosure.

An example of the ability of an array lens type of epithelial lenticule to have a multifocal effect is shown by the scans in FIGS. 7-12 as well as in the chart of FIG. 13. FIGS. 7-9 illustrate the condition of eye of the example after multiple refractive surgery procedures and FIGS. 10-12 illustrate the condition of this eye following a Photo Therapeutic Keratectomy (PTK) smoothing procedure. The pre-op surface topography (FIG. 9) was relatively smooth, but the epithelial thickness profile (FIGS. 7 and 8) demonstrates a multi-ring lenticular configuration 402, which is a type of epithelial lens array. Clinically, the patient had very low contrast sensitivity before the operation, which could be explained by the detrimental effect of an excessive multifocal epithelial lenticule. An excimer laser trans-epithelial PTK smoothing procedure was performed, which regularized the epithelial thickness and improved contrast sensitivity as can be seen in the corresponding topography scans and sections shown in FIGS. 10-13. This case demonstrates the detrimental effect of excessive multifocality and that induced epithelial multifocal lenticules should be limited to those that remain sub-surface, i.e. where the epithelium has fully or nearly fully compensated for the underlying irregularity.

Embodiments of the present invention are particularly advantageous for presbyopic treatments in which various factors may be used to create a protocol for the presbyopic treatments. The ablation profiles described above can be used to increase the depth of field in each eye of a presbyopic patient, which partially counteracts the effects of presbyopia. These ablation profiles are not currently able to increase the depth of field to restore the full range of vision in a single eye, therefore, a certain degree of monovision can be used to achieve clear binocular vision at both near, intermediate and far distances. However, due to the increased depth of field in both eyes, a lower degree of anisometropia can be used compared with traditional monovision. Such monovision with a lower degree of anisometropia is referred to herein as micro-monovision. In an embodiment, the standard micro-monovision protocol targets to correct the dominant eye to approximately plano and the non-dominant eye to approximately −1.50 D irrespective of age. The depth of field of the predominantly distance (dominant) eye enables it to see at distance down to intermediate, while the predominantly near (non-dominant) eye is able to see in the near range and up to intermediate. In the intermediate region both eyes have similar acuity, which draws on the natural neural process of binocular fusion.

It can also be advantageous to test the patients preoperatively to assess their tolerance for anisometropia of 1.50 D. If the patient cannot tolerate 1.50 D, an iterative process can be followed by retesting the patient by reducing the anisometropia, for example, in 0.25 D steps until the patient reports no cross blurring. An alternative method is to use the following protocol for subjects that are less tolerant to monovision. The target refractions are adjusted depending on the subject's age such that the dominant eye target is graded from plano at age 45 to −0.50 D for ages 65 and over, and the non-dominant eye target is graded from −0.75 D at age 45 to −1.25 D for 65 and over.

The higher order aberration component of the ablation profile can also be adjusted according to the age of the patient. As presbyopia increases as age increases, older patients can benefit more than younger patients from an increase in depth of field and the presence of a multi-focal epithelial lenticule.

For example, an additional $Z_4^0$ could be included depending on age of about −0.25 μm at age 40 up to about −1.00 μm at age 70.

Having accounted for the variables of the refraction to be treated, the preoperative higher order aberration and the patient's age, the total pre-compensating component, such as the total $Z_4^0$ can be calculated based on a sum of the $Z_4^0$ addition corresponding to each variable so as to yield an ideal $Z_4^0$ amount to be included in the ablation profile in order to shift the spherical aberration to within the beneficial range without exceeding the tolerable threshold. Relative to the ideal, the amount of $Z_4^0$ included can be limited to an upper limit of −2.75 μm to avoid the creation of central islands, as described earlier. An additional factor is the balance between the accuracy of the refractive correction and the expectation of each patient. Including a large $Z_4^0$ component in the ablation profile can reduce the accuracy of the refractive correction, while patients with lower preoperative refractions tend to have higher expectations as the patient already has reasonably good vision. Therefore, the maximum limit applied on the $Z_4^0$ component can be adjusted according to the refraction treated with a lower limit for lower corrections. Moreover, the maximum limit can be higher for the non-dominant (near vision) eye as the accuracy of the treatment of the non-dominant eye has less impact on the patient's vision than the dominant (distance vision) eye.

A further component is the increase in depth of field afforded by pupil constriction during accommodation: a component that persists even in eyes that have lost the ability to change crystalline lens power during the accommodative effort. The combination of controlled induced corneal aberrations and pupil constriction gives a significant increase in depth of field on the retinal image, albeit not a perfect image.

In eyes with a large angle kappa, the angle between the line of sight (line joining the fixation point and the centre of the entrance pupil) and the visual axis is increased. This implies that the line of sight and the visual axis will intersect the cornea at two separate points and the distance between the two points in the corneal plane increases for larger angles kappa. In such eyes with large angle kappa, the choice of the location of the ablation centre and therefore the location of spherical aberration induction is even more relevant. For example, induction of spherical aberration on the corneal vertex will result in induction of coma on the pupil centre because of the distance between the two points. Because almost all aberrometers measure aberrations with reference to the pupil centre (and not the corneal vertex), centration of the ablation profile on the corneal vertex and induction of SA on the corneal vertex as described in this method, will be wrongly measured with most aberrometers as an induction in coma. Similarly, induction of coma on the pupil centre may result in induction of spherical aberration on the corneal vertex.

In certain embodiments, the lens shown in FIG. 1 102 may include an intraocular lens implanted in the eye in accordance with known implantation procedures. Embodiments of the invention are described in detail below relative to various elements shown in FIG. 1.

In one embodiment, the method disclosed herein is applied to adjust corneal aberrations along the visual axis together with any remaining refractive error (cylinder in particular) following cataract surgery. For example, corneal spherical aberration gives increased depth of field, therefore enabling patients to see at near and far binocularly despite, for example, the presence of a monofocal IOL. Monofocal IOLs are safer (less Posterior Capsular Opacification) and do not induce night vision disturbances or reduce contrast sensitivity—all compromises which are produced by multifocal IOLs. For example, a post cataract patient who was left plano in both eyes would need +3.00 to read. With managing the spherical aberration on the cornea one can produce an increase in depth of field in both eyes so that the dominant eye can see distance to intermediate and the non-dominant eye can see intermediate to near, with approximately 1.50 D of anisometropia.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of for performing a corneal ablation procedure on the eyes of a patient, the method comprising:
   determining a first refractive correction for a first eye;
   determining a first parameter corresponding to at least one of the first refractive correction and a condition of the patient;
   selecting a first ablation profile for the first eye including a first refractive correction component and a first pre-compensating component, the first pre-compensating component being selected based on the first parameter, the first ablation profile being configured so as to promote a controlled induction of a higher order aberration, wherein the first pre-compensating component limits the induction of the higher order aberration to be within a first predefined range;

determining a second refractive correction for a second eye, the second refractive correction being different than the first refractive correction;

determining a second parameter corresponding to at least one of the second refractive correction and a condition of the patient;

selecting a second ablation profile for the second eye including a second refractive correction component and a second pre-compensating component, the second pre-compensating component being selected based on the second parameter, the second ablation profile being configured so as to promote a controlled induction of a higher order aberration, wherein the second pre-compensating component limits the induction of the higher order aberration to be within a predefined range; and ablating the cornea of the eyes with an excimer laser unit using the selected first and second ablation profiles so as to carve a ring paracentrally in a stroma layer of the cornea;

wherein the ablation of at least one of the first and second eyes results in an epithelial lenticule forming by filling in the carved ring in the stroma layer, the epithelial lenticule having sub-surface multi-focal properties as a result of the pre-compensating component of the respective ablation profile; and wherein the forming of the epithelial lenticule renders a front corneal surface to be regular and without multi-focal properties.

2. The method recited in claim 1, wherein the first and second refractive corrections are determined so as to produce anisometropia of about 1.5 D.

3. The method recited in claim 1, wherein the first and second refractive corrections are determined so as to produce an amount of anisometropia based on a monovision tolerance of the patient.

4. The method recited in claim 1, wherein at least one of the first and second eyes includes an intraocular lens.

* * * * *